US012653630B2

(12) United States Patent
Tetsuka et al.

(10) Patent No.:     US 12,653,630 B2
(45) Date of Patent:         Jun. 16, 2026

(54) X-RAY DIAGNOSTIC APPARATUS AND X-RAY DIAGNOSTIC SYSTEM

(71) Applicant: CANON KABUSHIKI KAISHA, Tokyo (JP)

(72) Inventors: Akio Tetsuka, Shioyagunshioyamachi (JP); Masaki Kobayashi, Otawara (JP); Yoshiyuki Sato, Nasushiobara (JP); Keisuke Nakamura, Utsunomiya (JP); Kenji Mizutani, Nasushiobara (JP); Akihito Takahashi, Nasushiobara (JP); Shingo Abe, Nasushiobara (JP); Mitsuru Sakata, Yaita (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 115 days.

(21) Appl. No.: 18/673,592

(22) Filed: May 24, 2024

(65) Prior Publication Data

US 2024/0398491 A1      Dec. 5, 2024

(30) Foreign Application Priority Data

May 31, 2023      (JP) ............................. JP2023-089748

(51) Int. Cl.
*A61B 34/30*          (2016.01)
*A61B 6/00*            (2006.01)
(Continued)

(52) U.S. Cl.
CPC ................ *A61B 34/30* (2016.02); *A61B 6/12* (2013.01); *A61B 6/4441* (2013.01); *A61B 6/461* (2013.01);
(Continued)

(58) Field of Classification Search
CPC ......... A61B 6/12; A61B 6/4441; A61B 6/461; A61B 6/487; A61B 6/503; A61B 6/541; A61B 34/30; A61B 2034/301
See application file for complete search history.

(56) References Cited

U.S. PATENT DOCUMENTS

| | | | | |
|---|---|---|---|---|
| 10,736,588 | B2 * | 8/2020 | Van Dijk | ................ A61B 6/542 |
| 2014/0029722 | A1 * | 1/2014 | Matsumoto | .......... A61B 6/4441 |
| | | | | 378/62 |

(Continued)

FOREIGN PATENT DOCUMENTS

JP          2019-502444 A      1/2019

*Primary Examiner* — Mark R Gaworecki
(74) *Attorney, Agent, or Firm* — Oblon, McClelland, Maier & Neustadt, L.L.P.

(57)          ABSTRACT

In one embodiment, an X-ray diagnostic apparatus can communicate with a controller configured to operate a catheter robot capable of moving an inserted device within the object and comprises a display and processing circuitry. The display is configured to display at least one fluoroscopic image of an object. The processing circuitry is configured to receive a control signal indicating a content of an operation on the catheter robot from the controller, acquire a plurality of fluoroscopic images of the object by irradiating the object with X-rays, control X-ray irradiation to the object, cause the display to display the plurality of fluoroscopic images to be sequentially acquired when the X-ray irradiation is performed, generate a plurality of reproduced images based on the plurality of fluoroscopic images acquired before a stop of the X-ray irradiation and cause the display to display the plurality of reproduced images when the X-ray irradiation is stopped.

20 Claims, 5 Drawing Sheets

(51) Int. Cl.
    *A61B 6/12*          (2006.01)
    *A61B 6/46*          (2024.01)
    *A61B 6/50*          (2024.01)

(52) U.S. Cl.
    CPC .............. *A61B 6/487* (2013.01); *A61B 6/503*
                (2013.01); *A61B 6/541* (2013.01); *A61B*
                         *2034/301* (2016.02)

(56)              References Cited

U.S. PATENT DOCUMENTS

2017/0181718 A1*   6/2017   Akiyama ............... A61B 6/487
2018/0360398 A1   12/2018   Wenderow et al.
2019/0320991 A1*   10/2019   Yoshida ................. A61B 6/463
2022/0202381 A1   6/2022   Wenderow et al.

* cited by examiner

200 X-RAY DIAGNOSTIC APPARATUS

6 ROBOTIC ASSISTANT APPARATUS

CONSOLE 60

61 DISPLAY

TOUCH SCREEN 621

62 CONTROLLER

63 TABLE

BUTTON 624

623 BUTTON

622 JOYSTICK

64 FOOT SWITCH

X-RAY DIAGNOSTIC APPARATUS AND X-RAY DIAGNOSTIC SYSTEM

CROSS-REFERENCE TO RELATED APPLICATION

This application is based upon and claims the benefit of priority from Japanese Patent Application No. 2023-089748 filed on May 31, 2023, the entire contents of which are incorporated herein by reference.

FIELD

Disclosed embodiments relate to an X-ray diagnostic apparatus and an X-ray diagnostic system.

BACKGROUND

A robotic catheter system assists a doctor in performing a catheterization such as PCI (Percutaneous Coronary Intervention), and such a robot for assisting the doctor in performing a medical procedure is hereinafter referred to as a "catheter robot". For example, the catheter robot can insert a device such as a catheter into an object such as a patient and move the device within the object. When the doctor or another user operates a robot console installed near the X-ray diagnostic apparatus such as an X-ray angiography apparatus or installed at a remote location away from the X-ray diagnostic apparatus, the device inserted into the object, such as a catheter, can be moved by the catheter robot.

Normally, the catheter robot is operated at the same time as X-ray imaging using the X-ray diagnostic apparatus such as an X-ray angiography apparatus. For example, the X-ray diagnostic apparatus irradiates the object with X-rays to time-sequentially generate fluoroscopic images in real-time such that the doctor can observe the movement of the vascular system and the movement and current position of the catheter to be moved by the catheter robot. In such a case, there is a known technique that reduces the radiation exposure of the object and the doctor by lowering the X-ray frame rate in accordance with the movement of the catheter and the vascular system.

However, if the X-ray frame rate is lowered with respect to the organs having movements such as the heart, it becomes impossible to observe movement smoothly. Furthermore, even if the X-ray frame rate is lowered, since X-rays continues to be irradiated, the object and/or the doctor will continue to be exposed to radiation.

As compared with a usual catheterization directly performed by the doctor (i.e., manual surgical operation by the doctor), the doctor has difficulty operating the catheter robot intuitively. Thus conceivably, it takes more time for the doctor to check the current position of the tip of the catheter. Hence, even if the dose of X-ray irradiation is reduced during the time the doctor checks the current position of the tip of the catheter, the radiation exposure during the check period cannot necessarily be reduced.

DETAILED DESCRIPTION

Hereinbelow, embodiments of an X-ray diagnostic apparatus and an X-ray diagnostic system will be described in detail by referring to the accompanying drawings.

In one embodiment, an X-ray diagnostic apparatus can communicate with a controller configured to operate a catheter robot capable of inserting a device into an object and moving the device within the object and comprises a display and processing circuitry. The display is configured to be able to display at least one fluoroscopic image of an object. The processing circuitry is configured to receive a control signal indicating a content of an operation on the catheter robot from the controller, acquire a plurality of fluoroscopic images of the object by irradiating the object with X-rays, control X-ray irradiation to the object, cause the display to display the plurality of fluoroscopic images to be sequentially acquired when the X-ray irradiation is performed, generate a plurality of reproduced images based on the plurality of fluoroscopic images acquired before a stop of the X-ray irradiation and cause the display to display the plurality of reproduced images when the X-ray irradiation is stopped.

First Embodiment

Figure 1:
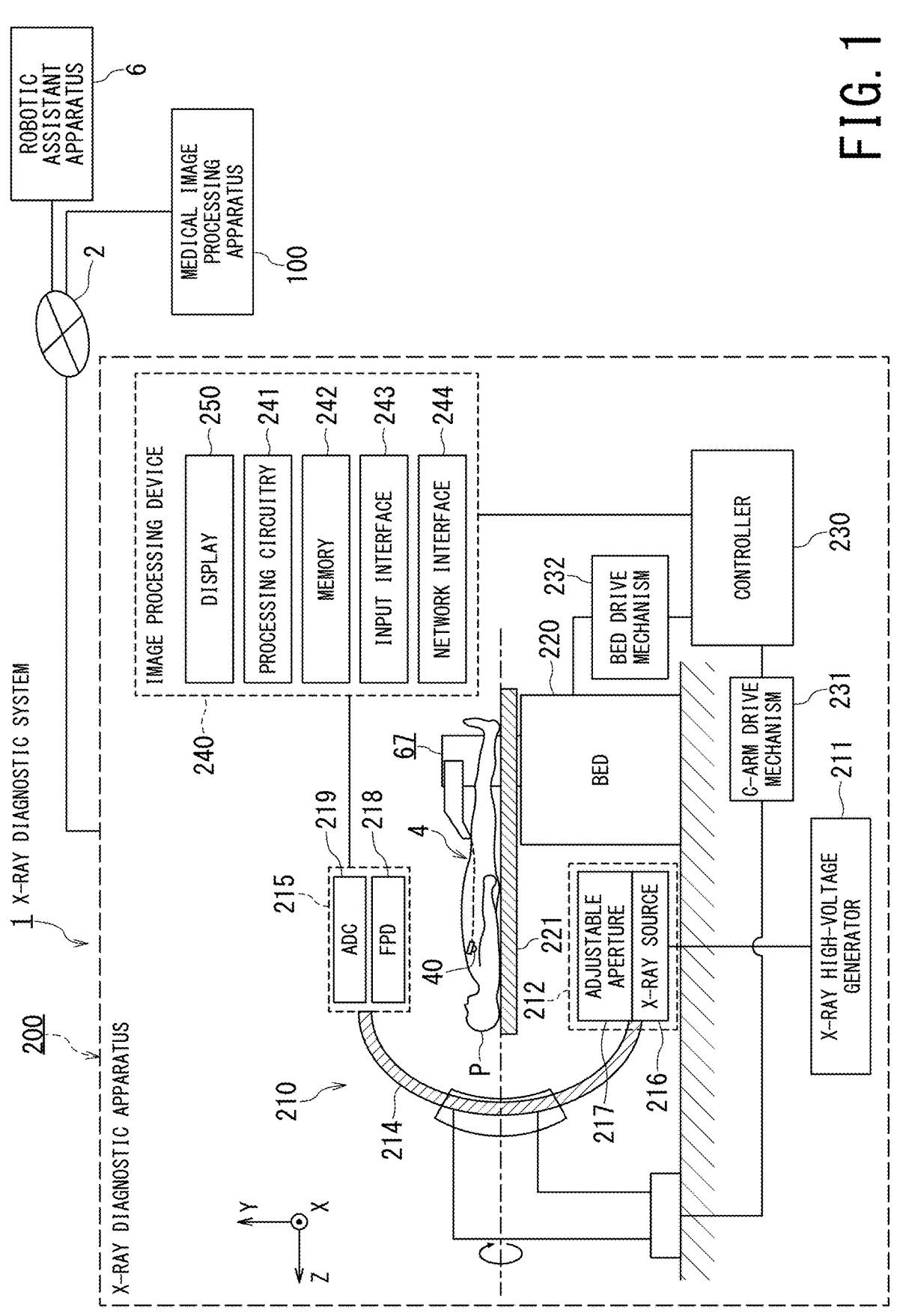
FIG. 1 is a block diagram illustrating a configuration of an X-ray diagnostic system according to the first embodiment.
Figure 2A:
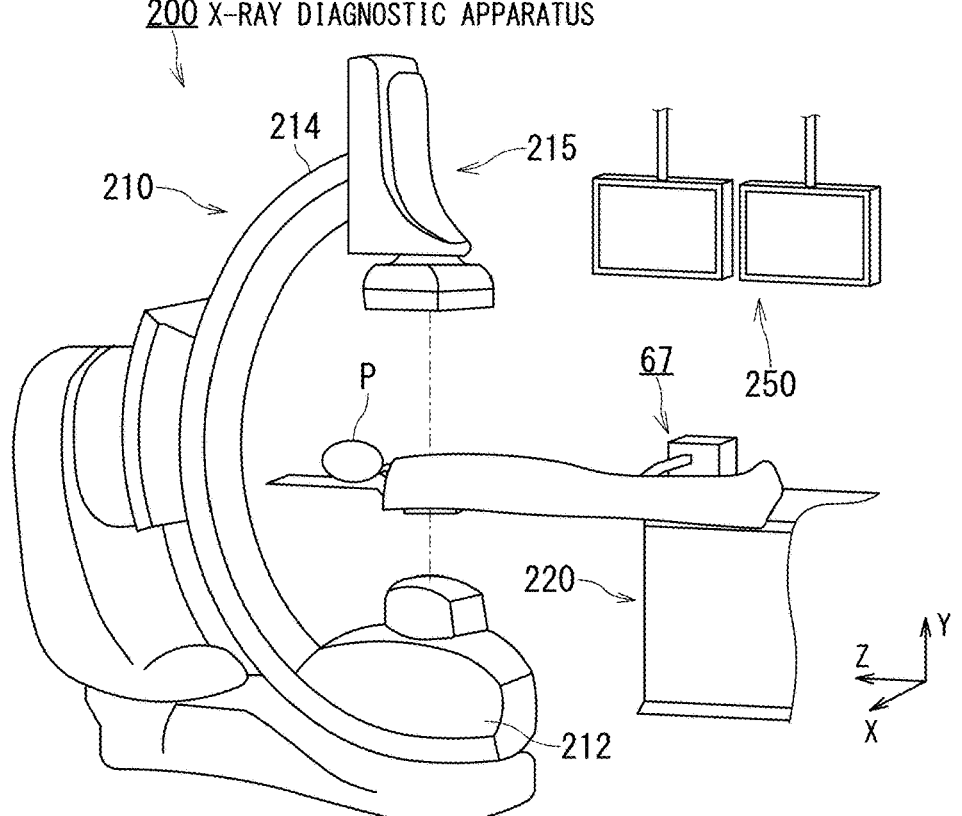
FIG. 2A is a perspective view illustrating an appearance of an X-ray diagnostic apparatus according to the first embodiment.

FIG. 1 is a block diagram illustrating a configuration of an X-ray diagnostic system 1 that includes an X-ray diagnostic apparatus 200 according to the first embodiment. FIG. 2A is a perspective view illustrating an appearance of the X-ray diagnostic apparatus 200 according to the first embodiment.

As shown in FIG. 1, the X-ray diagnostic system 1 includes a medical image processing apparatus 100, the X-ray diagnostic apparatus 200, and a robotic assistant apparatus 6. These apparatuses are communicably connected to each other via a network 2.

The X-ray diagnostic apparatus 200 includes a scanner 210, a bed 220, a controller 230, and an image processing device 240. The scanner 210, the bed 220, and the controller 230 are generally installed in an operating room (i.e., an examination room or a treatment room), and the image processing device 240 is installed in a control room adjacent to the operating room.

The scanner 210 includes an X-ray high-voltage generator 211, an X-ray irradiator 212, a table (i.e., a table for a catheterization) 221, a C-arm 214, an X-ray detector 215, a C-arm drive mechanism 231, and a bed drive mechanism 232.

The X-ray irradiator 212 is provided at one end of the C-arm 214. The X-ray irradiator 212 is provided so as to be able to rotate and move in an arc under the control of the controller 230. The X-ray irradiator 212 includes an X-ray source 216 (for example, an X-ray tube) and an adjustable aperture 217. The X-ray source 216 is supplied with high-voltage power from the X-ray high-voltage generator 211, and generates X-rays in accordance with the conditions of the high-voltage power. The adjustable aperture 217 movably supports aperture blades made of an X-ray shielding material at an X-ray irradiation port of the X-ray source 216.

The X-ray detector 215 is provided at the other end of the C-arm 214 so as to face the X-ray irradiator 212. The X-ray detector 215 is provided so as to be able to rotate and move in an arc under the control of the controller 230. The X-ray detector 215 includes an FPD (Flat Panel Detector) 218 and an ADC (Analog to Digital Converter) 219.

The FPD 218 has a plurality of detection elements arranged in two dimensions. Between the respective detection elements of the FPD 218, scanning lines and signal lines are arranged so as to be orthogonal to each other. Note that a grid may be provided on the front of the FPD 218.

The ADC 219 converts projection data of time-sequential analog signals (i.e., video signal) outputted from the FPD 218 into digital signals, and outputs the digitalized time-sequential projection data to the image processing device 240.

As shown in FIG. 2A, the C-arm 214 disposes both the X-ray irradiator 212 and the X-ray detector 215 in such a manner that both face each other with an object P interposed in the middle of both. As shown in FIG. 1, under the control of the controller 230, the C-arm 214 integrally rotates both the X-ray irradiator 212 and the X-ray detector 215 and moves both in the arc direction of the C-arm 214 by the C-arm drive mechanism 231. In the following, a description will be given of a case where the X-ray diagnostic apparatus 200 is provided with the C-arm 214 and this C-arm 214 integrally drives the X-ray irradiator 212 and the X-ray detector 215.

The bed 220 is supported by the floor and supports the table 221. Under the control of the controller 230, the bed 220 can slide the table 221 (in the X-axis and Z-axis directions), lift and lower the table 221 (in the Y-axis direction), and roll the table 221 by the bed drive mechanism 232. Although a description will be given of an under-tube type scanner 210 in which the X-ray irradiator 212 is disposed below the table 221, the scanner 210 may be configured as an over-tube system in which the X-ray irradiator 212 is disposed above the table 221.

The controller 230 includes a CPU (Central Processing Unit) and a memory (not shown). The controller 230 controls the driving of the X-ray irradiator 212, the X-ray detector 215, and the C-arm 214 of the scanner 210 as well as the driving of the bed 220 for positioning under the control of the image processing device 240. The controller 230 also controls the operation of each of the X-ray irradiator 212, the X-ray detector 215, and the C-arm drive mechanism 231 for X-ray radiographic imaging and/or X-ray fluoroscopic imaging under the control of the image processing device 240.

The image processing device 240 is configured based on a computer, and includes processing circuitry 241, a memory 242, an input interface 243, a network interface 244, and a display 250.

The processing circuitry 241 is a circuit that controls the operation of the entirety of the X-ray diagnostic apparatus 200, and controls the controller 230 by executing various programs read out from the memory 242 on the basis of an input from a user U via the input interface 243 and/or various data read out from the memory 242. In addition, the processing circuitry 241 generates X-ray images such as a fluoroscopic image and a radiographic image of the object P on the basis of the signals acquired by the scanner 210, and controls respective components such that the X-ray images for display stored in the memory 242 are displayed on the display 250, for example.

The memory 242 stores: image data; various data such as diagnostic information and diagnostic protocols; and various programs for the control by the controller 230, for image processing, and for display processing, for example. The memory 242 is achieved by an optical disk, a hard disk, and a semiconductor memory element such as a RAM (Random Access Memory) and a flash memory, for example.

The network interface 244 is an interface for communicating with various apparatuses connected to the network 2 by wire or wirelessly. For example, the X-ray diagnostic apparatus 200 can exchange various data and images with the medical image processing apparatus 100 and the robotic assistant apparatus 6 through the network interface 244.

The input interface 243 includes: an input device that can be operated by the user U; and an input circuit that receives signals from the input device. The input device can be achieved by a mouse, a keyboard, a touchpad that performs input operations by touching an operation surface, a touchscreen in which a display screen and a touchpad are integrated, a non-contact input circuit using an optical sensor, and a voice input circuit, for example.

The display 250 displays a GUI (Graphical User Interface) for receiving an instruction from the user U through the input interface 243 and X-ray images generated by the image processing device 240, for example. The display 250 also displays various messages and display information to notify the user U of the processing status and processing results of the X-ray diagnostic apparatus 200. In addition, the display 250 may have a speaker and output audio. Further, the display 250 can display various support images and/or support information generated by the medical image processing apparatus 100 for supporting operations on the catheter 4, as exemplified by data and images received from various apparatuses connected to the network 2.

FIG. 1 shows the catheter 4 and a medical device 40. In this specification, mainly, a thin medical device to be inserted into the body cavity of the object P or into a tubular tissue such as a blood vessel for treatment or diagnosis is referred to as the catheter 4. The catheter 4 includes, for example, a thin tube constituting its main body, a guidewire for guiding the catheter 4 to the treatment target site, and the medical device 40 attached to the tip of the catheter 4.

The medical device 40 is a part to be used for treatment at a predetermined target site after the catheter 4 is inserted into the body of the object P. Aspects of the medical device 40 include devices such as an occlusion device, a balloon, and a stent. As one case in the following description, the target site for treatment is assumed to be the heart and its surroundings.

The medical image processing apparatus 100 has the function of controlling the robotic assistant apparatus 6. The robotic assistant apparatus 6 is an apparatus that can perform an operation of inserting the catheter 4 into the object P and moving the catheter 4 to the treatment target site of the object P. This operation is performed on the basis of user operations on a console 60 that is installed remotely from the X-ray diagnostic apparatus 200. The robotic assistant apparatus 6 may be referred to as a robotic catheter system 6 or a catheter robot 6. The console 60 of the robotic assistant apparatus 6 may be located at a remote location different from the operating room or may be located inside the operating room. The robotic assistant apparatus 6 is one example of a catheter robot.

Figure 2B:
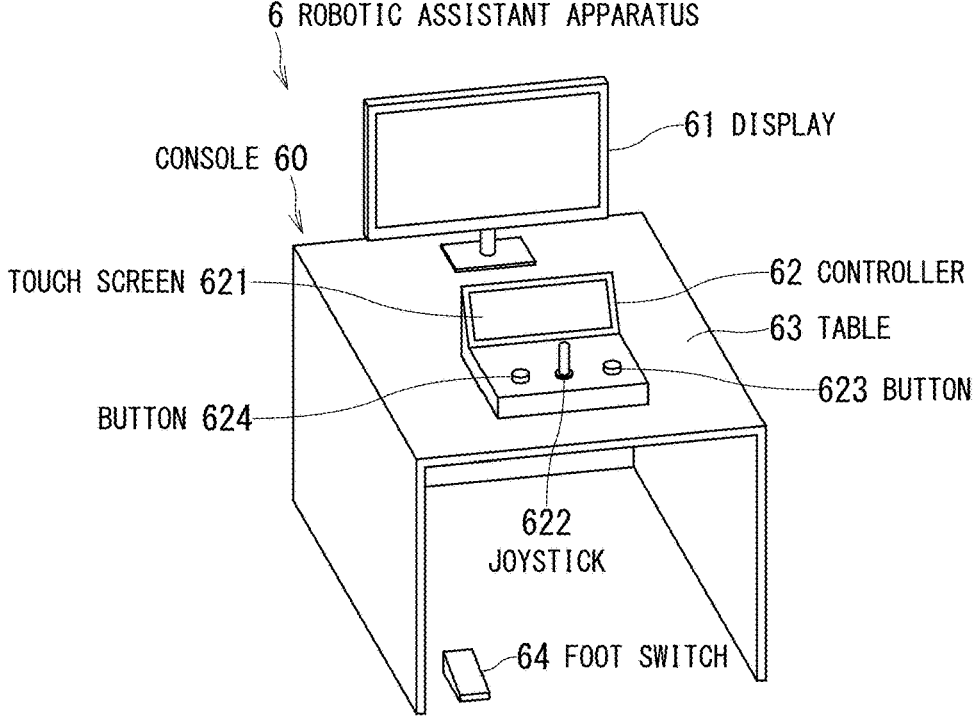
FIG. 2B is a perspective view illustrating an appearance of a console of a robotic assistant apparatus according to the first embodiment.

FIG. 2B is a perspective view illustrating an appearance of the console 60 of the robotic assistant apparatus 6. As shown in FIG. 1 and FIG. 2B, the robotic assistant apparatus 6 includes the console 60 and a robot main-body 67. The robot main-body 67 is disposed near the bed 220, and can insert the catheter 4 into the object P and move the catheter 4 to the treatment target site within the object P.

The console 60 includes a display 61, a controller 62, a table 63, and a foot switch 64. The display 61 and the controller 62 are disposed on the table 63, for example. The foot switch 64 is disposed under the table 63, for example.

The display 61 displays information or patient-specific data to the user near the console 60. For example, the display 61 displays X-ray images, CT images, hemodynamic data such as blood pressure and heart rate, and patient record information such as a medical history, age, and weight. In addition, the display 61 displays procedure-specific information such as duration of the procedure, a catheter position, a guidewire position, and volume of a delivered drug or a delivered contrast agent. The display 61 also displays information on the position of the catheter 4.

The display 61 may display the same image as the image displayed on the display 250 of the X-ray diagnostic apparatus 200 (for example, a fluoroscopic image and a reproduced image described below).

The controller 62 is a device for operating the robotic assistant apparatus 6 that can insert the catheter 4 into the object P and move the catheter 4 within the object P. For example, the controller 62 can be configured to: advance, retreat, or rotate the catheter 4; inflate or deflate a balloon installed on the catheter 4; place and deploy a stent; inject a contrast medium into the catheter 4; and inject a drug into the catheter 4. The controller 62 can implement various other functions that may be part of a medical procedure based on the catheter 4. In order to achieve this, the controller 62 may be configured to cause the robot main-body 67 to perform various tasks with the use of various percutaneous intervention devices that may be provided in the robot main-body 67.

The controller 62 includes a touch screen 621, a joystick 622, and buttons 623 and 624. The touch screen 621 displays one or more icons (not shown) related to the respective components of the controller 62. For example, the joystick 622 is configured to advance, retract, or rotate various components and percutaneous devices including the catheter 4. For example, corresponding to the direction and amount (angle) of the joystick 622 operated by the user U, the components and the percutaneous devices operate. The buttons 623 and 624 may include a button for selecting a reproduction speed of many frames of time-sequential images, for example.

The foot switch 64 is a switch that allows the user U to turn on or turn off X-ray irradiation with his/her foot. The foot switch 64 is one example of an operation switch. The foot switch 64 may be installed near the bed 220. In this case, the switching operation of turning on or turning off the X-ray irradiation with the use of the foot switch 64 may be performed by another user other than the user U of the console 60.

Figure 3:
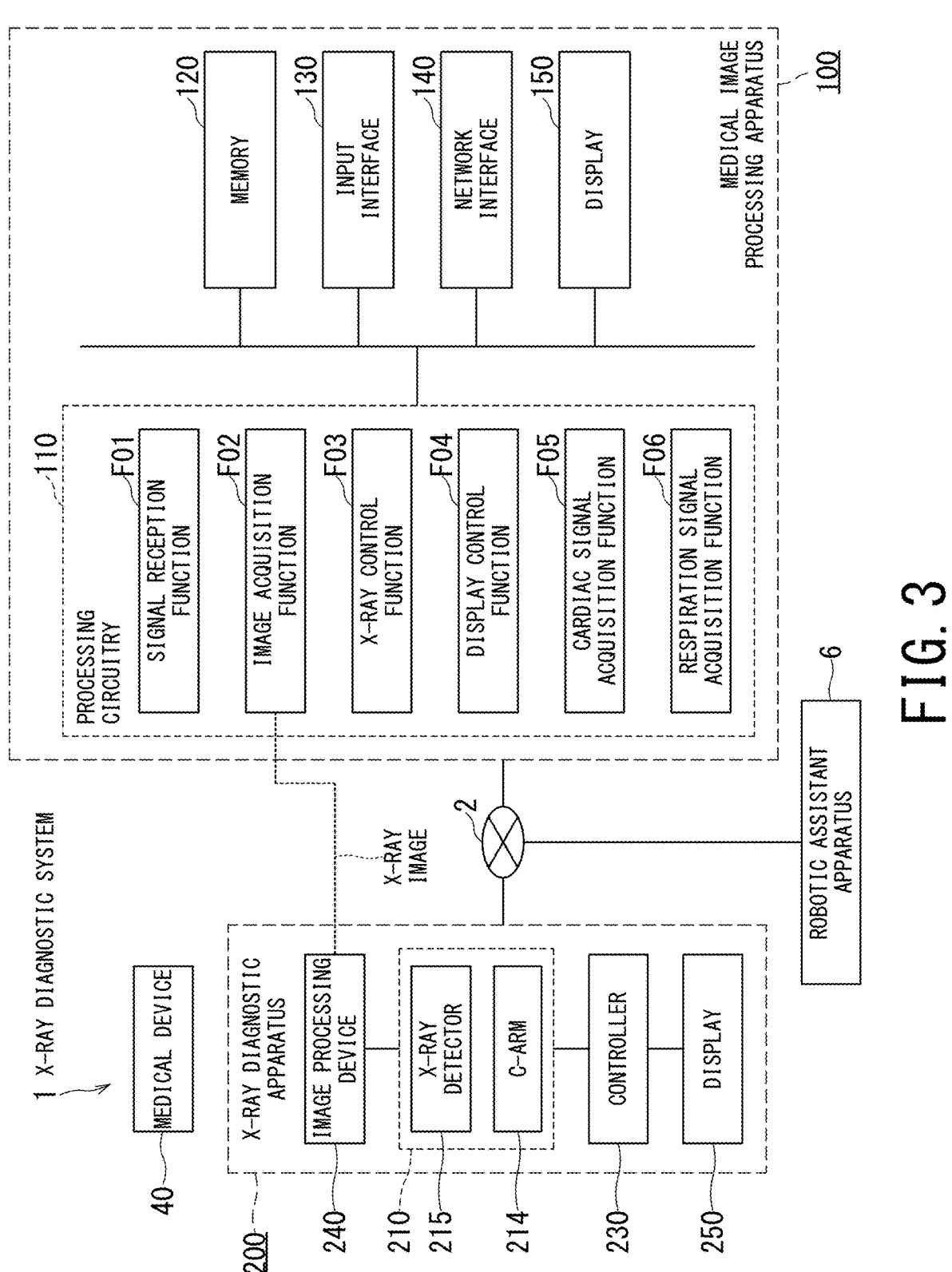
FIG. 3 is a block diagram illustrating a configuration of a medical image processing apparatus according to the first embodiment.

FIG. 3 is a block diagram illustrating a configuration of the medical image processing apparatus 100 according to the first embodiment. As shown in FIG. 3, the medical image processing apparatus 100 is configured to be able to communicate with the X-ray diagnostic apparatus 200 and the robotic assistant apparatus 6 via the network 2. The medical image processing apparatus 100 is configured as a computer such as a workstation and a personal computer. The medical image processing apparatus 100 provides the user U with images and information for supporting operations on the robotic assistant apparatus 6.

The medical image processing apparatus 100 includes processing circuitry 110, a memory 120, an input interface 130, a network interface 140, and a display 150. These components may be included in the image processing device 240 of the X-ray diagnostic apparatus 200. In other words, the entire system of the first embodiment may be configured such that the X-ray diagnostic apparatus 200 includes the above-described components of the medical image processing apparatus 100 and these components implement the respective functions described below. In this case, the X-ray diagnostic apparatus 200 can communicate with the controller 62.

The processing circuitry 110 has a special-purpose or general-purpose processor, and implements various functions described below through software processing by executing programs stored in the memory 120. The processing circuitry 110 may include hardware such as an Application Specific Integration Circuit (ASIC) and a programmable logic device such as a Field Programmable Gate Array (FPGA). The various functions described below can also be achieved by hardware processing using these components. In addition, the processing circuitry 110 may achieve the various functions described below by combining software processing and hardware processing.

The processing circuitry 110 implements each of a signal reception function F01, an image acquisition function F02, an X-ray control function F03, a display control function F04, a cardiac signal acquisition function F05, and a respiration signal acquisition function F06.

The signal reception function F01 includes a function to receive a control signal indicative of the operational detail by the user U on the robot main-body 67 from the controller 62.

The image acquisition function F02 includes a function to acquire fluoroscopic images of the object P by irradiating the object P with X-rays.

The X-ray control function F03 controls X-ray irradiation to the object P. The X-ray control function F03 includes a function to: perform the X-ray irradiation when the control signal indicates that the catheter 4 is moving inside the object P; and stop the X-ray irradiation when the control signal indicates that the catheter 4 is stopped inside the object P. The catheter 4 is one example of a device.

The display control function F04 includes a function to time-sequentially display a plurality of fluoroscopic images acquired in real time on the display 250 while the X-ray irradiation is being performed. In the meantime, when the X-ray irradiation is stopped, the display control function F04 includes a function to generate a plurality of reproduced images based on the plurality of fluoroscopic images acquired before a stop of the X-ray irradiation and display the plurality of reproduced images on the display 250.

The cardiac signal acquisition function F05 includes a function to acquire a cardiac signal (i.e., electrocardiographic waveform) of the object P from an electrocardiograph (not shown) attached to the object P. The cardiac signal is one example of electrocardiographic information.

The respiration signal acquisition function F06 includes a function to acquire a respiration signal of the object P from a respiratory sensor (not shown) such as a microwave Doppler sensor. The respiration signal is one example of respiration information.

The memory 25 is composed of, for example, a hard disk, an optical disk, and a semiconductor memory element such as a flash memory and a RAM. The memory 120 stores various processing programs (including application programs and an operating system, for example) to be used by the processing circuitry 110 and data necessary for executing the programs. In addition, the memory 120 can store various data such as image data inputted via the input interface 130 and/or the network interface 140.

The input interface 130 includes: an input device that can be operated by the user U; and an input circuit that receives signals from the input device. The input device can be achieved by a mouse, a keyboard, a touchpad that performs input operations by touching an operation surface, a touchscreen in which a display screen and a touchpad are integrated, a non-contact input circuit using an optical sensor, and a voice input circuit, for example.

The network interface 140 is an interface for communicating with various apparatuses connected to the network 2 by wire or wirelessly. For example, the medical image processing apparatus 100 can exchange various data with the X-ray diagnostic apparatus 200 and the robotic assistant apparatus 6 through the network interface 140.

The display 150 provides movement support information on the catheter 4 generated by the medical image processing apparatus 100 to the user U. For example, the display 150 may be a large-size display device disposed at a position where it can be easily viewed by the user U. The display 150 may have a speaker so as to be able to output the movement support information in audio form. In addition to the data such as the movement support information generated by the processing circuitry 110, the display 150 can also display data and images received from various apparatuses connected via the network 2 and various images generated by the medical image processing apparatus 100 for assisting the user U in operating the robotic assistant apparatus 6, for example.

Figure 4:
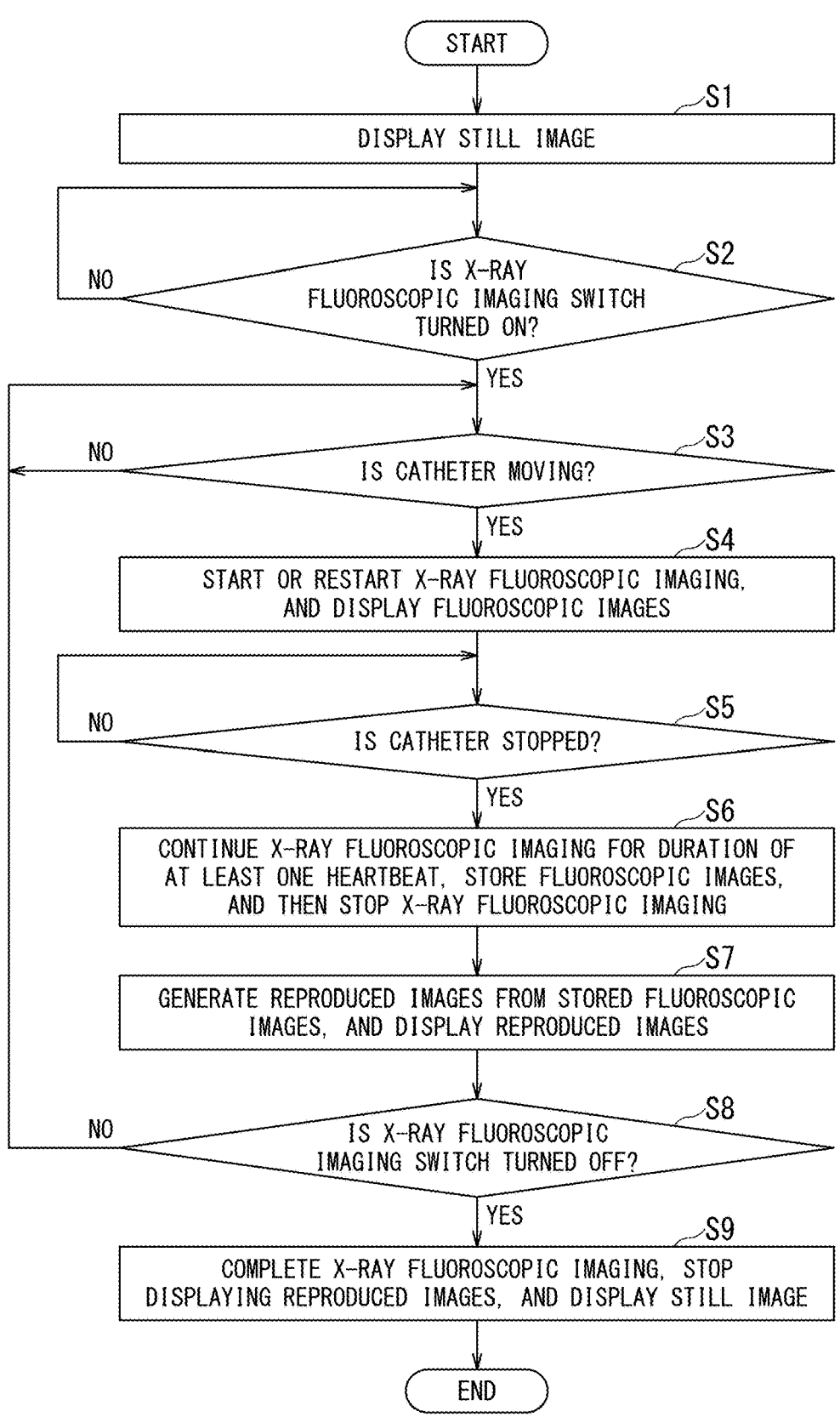
FIG. 4 is a flowchart illustrating processing to be performed by the medical image processing apparatus according to the first embodiment.

FIG. 4 is a flowchart illustrating the processing to be performed by the medical image processing apparatus 100 according to the first embodiment. This processing displays reproduced images or fluoroscopic images from X-ray fluoroscopic imaging for the user U, in accordance with the state of each switch. In the following, a description will be given of the processing in which the medical image processing apparatus 100 causes the display 250 of the image processing device 240 of the X-ray diagnostic apparatus 200 to display images. Note that the medical image processing apparatus 100 may cause the display 150 of the medical image processing apparatus 100 to display images or cause the display 61 provided on the console 60 of the robotic assistant apparatus 6 to display images.

Figure 5:
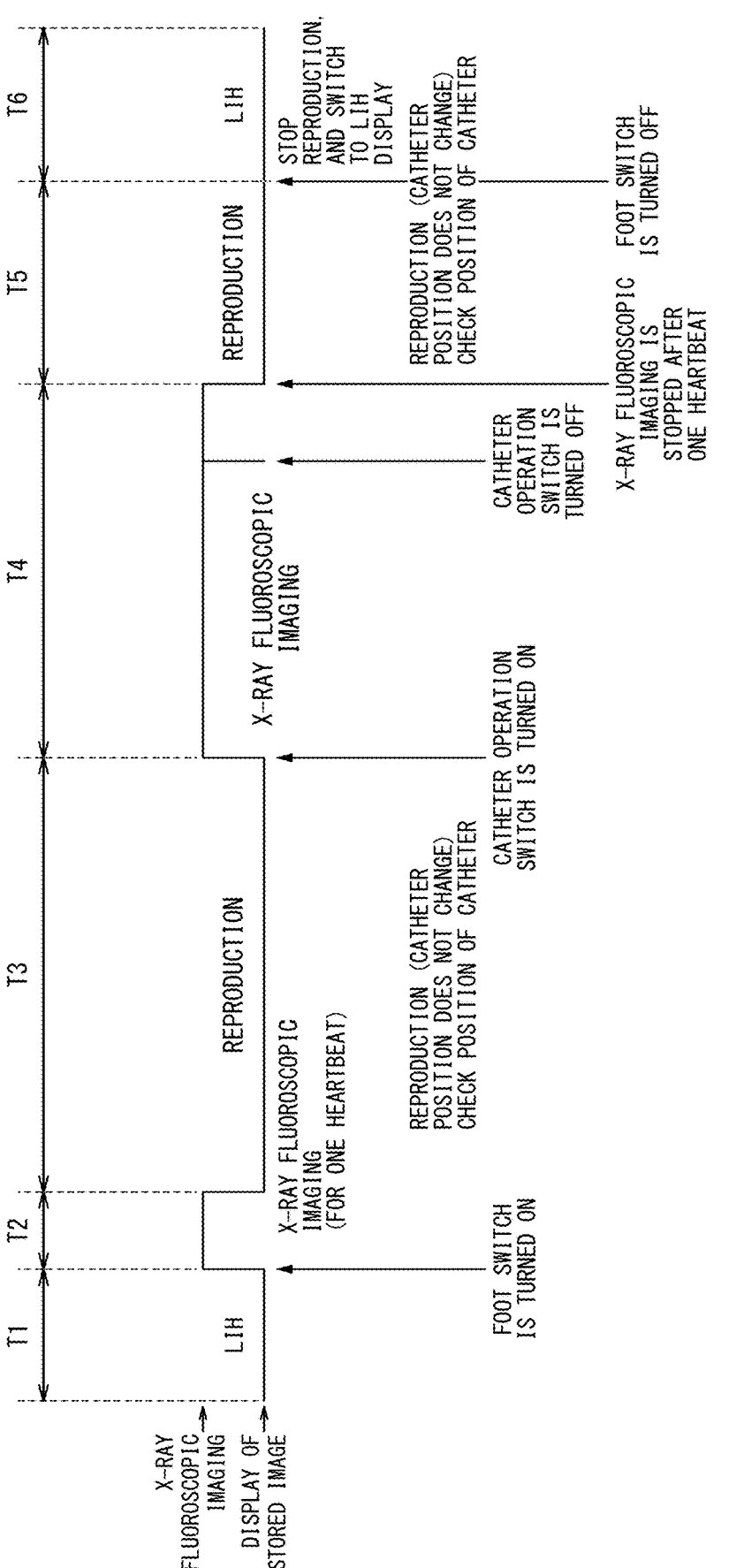
FIG. 5 is a timing chart illustrating the operation of the medical image processing apparatus or the X-ray diagnostic apparatus according to the first embodiment for each period.

FIG. 5 is a timing chart illustrating the operation of the medical image processing apparatus 100 or the X-ray diagnostic apparatus 200 according to the first embodiment for each of the plurality of periods Tn (n=1 to 6). In the timing chart of FIG. 5, the period during which the graph is at high level is the period during which X-ray irradiation to the object P is turned on and X-ray fluoroscopic imaging is performed. The period during which the graph is at low level is the period during which the X-ray irradiation to the object is turned off and X-ray fluoroscopic imaging is not performed.

In the period during which X-ray fluoroscopic imaging is performed, true (i.e., unprocessed) fluoroscopic images obtained by X-ray irradiation are time-sequentially displayed in real time. In the period during which X-ray fluoroscopic imaging is not performed, reproduced images (i.e., reproduced moving images) or a still image are generated from the stored fluoroscopic images and are displayed.

Hereinbelow, on the basis of FIG. 4 and FIG. 5, a description will be given of the processing in which the medical image processing apparatus 100 displays fluoroscopic images, reproduced images, and a still image.

In the step S1, the display control function F04 of the medical image processing apparatus 100 causes the display 250 of the X-ray diagnostic apparatus 200 to display a still image. This display of the still image is referred to as LIH (Last Image Hold). In the LIH, the display control function F04 displays the last frame image of the fluoroscopic images that are obtained from the most recent X-ray irradiation.

At the time of the step S1, it is assumed that the user U has not yet turned on the foot switch 64 configured as an X-ray fluoroscopic imaging switch and X-ray irradiation is not being performed. It is also assumed that the user U is not operating the controller 62 of the console 60 and the catheter 4 is stopped.

In the step S2, the processing circuitry 110 determines whether the foot switch 64 (i.e., the X-ray fluoroscopic imaging switch) is turned on or not. For example, when the user U depresses the foot switch 64, the foot switch 64 is turned on. If the foot switch 64 is turned on (YES in the step S2), the processing circuitry 110 advances the processing to the step S3. If the foot switch 64 is not turned on (NO in the step S2), the processing circuitry 110 repeats the processing of the step S2. The period T1 in FIG. 5 is the period from the start of displaying the still image in the step S1 to the turn-on determination of the foot switch 64 in the step S2.

In the step S3, the processing circuitry 110 determines whether the catheter 4 is moving or not. Specifically, the image acquisition function F02 receives the control signal indicating the operational detail of the robotic assistant apparatus 6 from the console 60. The processing circuitry 110 determines whether the received control signal indicates that the catheter 4 is moving within the object P or not. If the catheter 4 is moving (YES in the step S3), the processing circuitry 110 advances the processing to the step S4. If the catheter 4 is not moving (NO in the step S3), the processing circuitry 110 repeats the processing of the step S3.

According to the flowchart in FIG. 4, though the display of the still image by the step S1 continues while the step S3 is being repeated, processing different from this may be performed. For example, as shown in FIG. 5, when the foot switch 64 is turned on, X-ray fluoroscopic imaging may be temporarily performed during the period T2 equivalent to the length of one heartbeat of the object P so that reproduced images generated from the fluoroscopic images during this one heartbeat are displayed in the period T3 from the end of this temporary X-ray fluoroscopic imaging until the operation switch of the catheter 4 is turned on, i.e., until moving of the catheter 4 is started or restarted.

In the step S4, if the foot switch 64 being the X-ray fluoroscopic imaging switch is turned on (YES in the step S2) and the control signal indicates that the catheter 4 is moving within the object P (YES in the step S3), the X-ray control function F03 starts or resumes the X-ray irradiation to the object P. Since the X-ray irradiation is being performed, the display control function F04 causes the display 250 to time-sequentially display the fluoroscopic images sequentially acquired by the image acquisition function F02 on a real-time basis.

In the step S5, the processing circuitry 110 determines whether the catheter 4 is stopped or not. Specifically, the image acquisition function F02 receives the control signal indicating the operational detail of the robotic assistant apparatus 6 from the console 60. The processing circuitry 110 determines whether the control signal indicates that the catheter 4 is stopped within the object P or not. If the catheter 4 is stopped (YES in the step S5), the processing circuitry 110 advances the processing to the step S6. If the catheter 4 is not stopped (NO in the step S5), the processing circuitry 110 repeats the processing of the step S5.

In the step S6, the processing circuitry 110 continues X-ray fluoroscopic imaging for a period of at least one heartbeat (e.g., for a period of one heart beat) after the catheter 4 stops, stores the fluoroscopic images during this period, and then stops X-ray fluoroscopic imaging. For example, the X-ray control function F03 continues the X-ray irradiation to the object P for a period corresponding to at least one heartbeat of the object P on the basis of the timing synchronized with the cardiac signal. The image acquisition function F02 stores the fluoroscopic image data acquired during this period in the memory 120. Afterward, the X-ray control function F03 stops the X-ray irradiation. In other words, if the control signal indicates that the catheter 4 is stopped within the object P, the X-ray control function F03 stops the X-ray irradiation regardless of whether the foot switch 64 is turned on or turned off.

The period T4 in FIG. 5 is the period from the start/restart time of the X-ray irradiation by turning on the operation switch of the catheter 4 (i.e., by staring moving of the catheter 4) until the stop time of the X-ray irradiation after the operation switch of the catheter 4 is turned off (i.e., the catheter 4 is stopped), and then X-ray fluoroscopic imaging continues only for the period of at least one heartbeat.

In the step S7, the display control function F04 reads out the above-described plurality of fluoroscopic images for at least one heartbeat stored just before a stop of the X-ray irradiation from the memory 120, generates reproduced images from the fluoroscopic images, and displays the reproduced images on the display 250.

In the period during which the X-ray irradiation is stopped, the display control function F04 repeatedly reproduces the stored plurality of fluoroscopic images for at least one heartbeat (for example, a plurality of fluoroscopic images for the span equivalent to one heartbeat) so as to display them on the display 250. At this time, the display control function F04 may finely adjust (e.g., change, shorten, or extend) the reproduction cycle of the reproduced images (i.e., reproduction time of one cycle of cardiac images) corresponding to the heartbeat cycle based on the cardiac signal that is acquired by the cardiac signal acquisition function F05 (i.e., depending on the actual real-time heartbeat cycle of the object P). For example, the display control function F04 may finely adjust the reproduction cycle of the reproduced images in such a manner that the reproduction cycle of the reproduced images matches the heartbeat cycle based on the cardiac signal.

The heartbeat cycle of the object P can vary between the period during which the fluoroscopic images are acquired by X-ray fluoroscopic imaging and the period during which the reproduced images are displayed. Thus, the display control function F04 can make the heartbeat cycle of the reproduced images match the actual real-time heartbeat cycle of the object P by extending or shortening the display time-length of the reproduced images corresponding to the actual electrocardiogram waveform. For example, the display control function F04 can adjust the cardiac cycle of the fluoroscopic images to be reproduced, by shortening or extending the frame cycle of the fluoroscopic images to be reproduced.

The display control function F04 may display a mark indicating whether the image currently displayed on the display 250 is a reproduced image of a stored fluoroscopic image or a fluoroscopic image acquired in real time in such a manner that this mark is superimposed and displayed on the currently displayed image. Displaying such a mark can prevent the user U from being confused.

According to the processing in the steps S6 and S7, the user U can check the position of the catheter 4 without performing X-ray irradiation. In other words, according to the processing in the steps S6 and S7, while the object P is prevented from X-ray exposure, a sufficient time can be secured to determine whether the current position of the catheter 4 is at a proper position or not. In addition, deviation in the time axis between the reproduced images and the actual movement of the heart can be suppressed by synchronizing the display of the reproduced images with the cardiac signal.

The user U checks the position of the catheter 4 by observing the reproduced images, and then operates the joystick 622 or the other tool of the controller 62 to move the catheter 4 inside the blood vessel of the object P. At this time, X-ray fluoroscopic imaging is instantaneously restarted in conjunction with the control signal from the console 60, and the fluoroscopic images are time-sequentially displayed in real time. In other words, if the catheter 4 starts moving inside the object P after a stop of the X-ray irradiation due to a stop of the catheter 4 inside the object P, the X-ray control function F03 instantaneously restarts X-ray irradiation. This corresponds to the step S4 in the case of restarting the X-ray irradiation.

In the step S8, the processing circuitry 110 determines whether the foot switch 64 being the X-ray fluoroscopic imaging switch is turned off or not. For example, when the user U releases the foot switch 64, the foot switch 64 is turned off. If the foot switch 64 is turned off (YES in the step S8), the processing circuitry 110 advances the processing to the step S9. If the foot switch 64 is not turned off (NO in the step S8), the processing circuitry 110 returns the processing to the step S3.

In the period from the time at which the user U turns on the X-ray fluoroscopic imaging switch in the step S2 until the time at which the user U turns off the X-ray fluoroscopic imaging switch in the step S8, there is no manual on/off control of X-ray fluoroscopic imaging and the on/off control of X-ray fluoroscopic imaging is performed in conjunction with the robotic assistant apparatus 6. The period T5 in FIG. 5 is the period from the time at which X-ray fluoroscopic imaging is turned off due to a stop of the catheter 4 until the time at which the foot switch 64 being the X-ray fluoroscopic imaging switch is turned off. During the period T5, the reproduced images for one heartbeat are repeatedly displayed on the display 250 or the display 61, for example.

In the step S9, since the foot switch 64 has already been turned off by the user U, the X-ray control function F03 completes the X-ray irradiation to the object P accordingly. The display control function F04 stops displaying the reproduced images and switches the screen to display of a still image. This display of the still image is referred to as the LIH. In the LIH, the display control function F04 displays the last frame image of the fluoroscopic images generated by the X-ray irradiation just before its end. The period T6 is the period after the foot switch 64 being the X-ray fluoroscopic imaging switch is turned off, and is the period during which the still image is displayed.

According to the first embodiment, the X-ray irradiation to the object P can be suppressed to the minimum level without requiring any special operations by the user U. Further, by the electrocardiogram synchronous reproduction, natural reproduced images can be displayed without irradiating the object P with X-rays. This configuration can reduce the radiation exposure of the object P.

When the user U is a doctor, the user U needs time to check where the current catheter 4 is and to consider what operation to perform next while stopping the catheter 4 by operating the controller 62. This check and consideration period is assumed to be longer for robot operation than for manual operation (manipulation). During this check and consideration period, X-ray exposure of the object P can be stopped according to the first embodiment.

Second Embodiment

The medical image processing apparatus 100 or the X-ray diagnostic apparatus 200 according to the second embodiment differs from the first embodiment in the acquisition time of the fluoroscopic images. In the first embodiment, X-ray fluoroscopic imaging is performed for a duration of at least one heartbeat of the object P in the case of generating the reproduced images. However, when the treatment site or the examination site of the object with the use of the catheter 4 is not the heart, the acquisition time of the fluoroscopic images is not limited to the above-described aspect. The time length of acquiring the fluoroscopic images may be a predetermined time, an acquisition time corresponding to one frame of image, or a time corresponding to one breath of the object P, for example.

When the time length of acquiring the fluoroscopic images is a predetermined time, the fluoroscopic images of an anatomical imaging site except the heart, such as the brain which is an immovable part and/or lower limbs may be acquired.

When the time length of acquiring the fluoroscopic images is the time of one breath, in the step S7 of FIG. 4, the plurality of reproduced images are the plurality of fluoroscopic images for one breath of the object P and are acquired before a stop of X-ray irradiation. The display control function F04 repeatedly reproduces the plurality of fluoroscopic images for one breath so as to display them on the display 250 in the period during which the X-ray irradiation is stopped. This configuration can store the fluoroscopic images for a time length suitable for an anatomical imaging site except the heart, such as the liver and the abdomen, and can generate and display the reproduced images suitable for the liver and/or the abdomen.

In addition, the display control function F04 may adjust the reproduction cycle of the plurality of reproduced images corresponding to the respiration cycle based on the respiration signal that is acquired by the respiration signal acquisition function F06. The display control function F04 may adjust the reproduction cycle of the plurality of reproduced images in such a manner that the reproduction cycle of the plurality of reproduced images matches the respiration cycle based on the respiration signal, for example.

Further, the image acquisition function F02 may adjust the time length of acquiring the plurality of fluoroscopic images depending on a method of a surgical operation and an observation site. The observation site is one example of the target site of the object.

Third Embodiment

In the medical image processing apparatus 100 or the X-ray diagnostic apparatus 200 according to the third embodiment, reproduction speed of the reproduced images is different from the first embodiment and the second embodiment. The display control function F04 may switch the reproduction speed of the images to the recording speed or a slow speed. In other words, the display control function F04 may be able to arbitrarily adjust the reproduction speed of the plurality of reproduced images.

According to the third embodiment, the user U can view the reproduced images at a reproduction speed suitable for his/her eyes or at a reproduction speed suppressed as necessary. In addition, this configuration can meet the needs of the user U when it is preferred to carefully observe each reproduced image of the object P in terms of precise diagnosis or judgment.

Fourth Embodiment

The medical image processing apparatus 100 or the X-ray diagnostic apparatus 200 according to the fourth embodiment differs from the first to third embodiments in the content of the still image in the LIH display. In the step S9 of FIG. 4, when the X-ray irradiation is completed by turning off the foot switch 64 by the user U, the display control function F04 may select one frame image from the recorded frame images of one cardiac cycle and display the selected image as a still image on the display 250. For example, the display control function F04 may select one of: the fluoroscopic image most recently acquired by the image acquisition function F02; the reproduced image displayed on the display 250 at the time at which the X-ray irradiation is completed; and a reproduced image of an arbitrary heartbeat phase. The arbitrary heartbeat phase may be designated by the user U with the use of the controller 62.

Fifth Embodiment

The medical image processing apparatus 100 or the X-ray diagnostic apparatus 200 according to the fifth embodiment differs from the first to the fourth embodiments in that the X-ray irradiation is performed and stopped in conjunction with another event other than the movement and stop of the catheter 4. The X-ray diagnostic apparatus 200 may be able to further communicate with a driving apparatus, which drives a peripheral device except the console 60 or drives another medical apparatus except the X-ray diagnostic apparatus 200. In this case, the signal reception function F01 of the medical image processing apparatus 100 receives a driving signal indicating the content of the driving from the driving apparatus. If the driving signal indicates that the peripheral device or the other medical apparatus is being driven, the X-ray control function F03 performs the X-ray irradiation to the object P. If the driving signal indicates that the peripheral device or the other medical apparatus is not being driven, the X-ray control function F03 stops the X-ray irradiation.

For example, an injector configured to inject a contrast medium into the object P may be applied as the other peripheral device. In the case of injecting a contrast agent, the fluoroscopic images of the object P change sequentially (i.e., from image to image) due to the contrast agent, so the X-ray control function F03 performs the X-ray irradiation to the object P. If the contrast agent is not injected, the fluoroscopic images of the object P do not change between these images, so the X-ray control function F03 stops the X-ray irradiation to the object P.

In addition, the C-arm 214 and the bed 220 can be applied as the other peripheral devices. If the C-arm 214 rotates or moves in an arc or if the bed 220 slides, moves up and down, or rolls, the fluoroscopic images of the object P change sequentially (i.e., from image to image) due to change in the direction of X-ray irradiation or change in the target position, and thus, the X-ray control function F03 performs the X-ray irradiation to the object P. If both the C-arm 214 and the bed 220 are stopped, the fluoroscopic images of the object P do not change between these images, and thus, the X-ray control function F03 stops the X-ray irradiation to the object P.

Furthermore, an ultrasonic diagnostic apparatus may be applied as the other medical apparatus. If the ultrasonic diagnostic apparatus is being driven, the fluoroscopic images of the object P change sequentially (i.e., from image to image), and thus, the X-ray control function F03 performs the X-ray irradiation to the object P. If the ultrasonic diagnostic apparatus is not being driven, the fluoroscopic images of the object P do not change between these images, and thus, the X-ray control function F03 stops the X-ray irradiation to the object P.

Sixth Embodiment

The medical image processing apparatus 100 or the X-ray diagnostic apparatus 200 according to the sixth embodiment differs from the first to fifth embodiments in the function or configuration of the foot switch 64 that is an X-ray operation switch. For example, in the first and other embodiments, when the foot switch 64 is turned on, the X-ray irradiation is turned on under the condition that the catheter 4 is moving, and the X-ray irradiation is turned off when the catheter 4 is stopped. In other words, the foot switch 64 alone does not control on/off of the X-ray irradiation. Instead, the on/off of the X-ray irradiation is controlled by involving both the on/off state of the foot switch 64 and the moving/stopping state of the catheter 4.

The sixth embodiment is configured to enable selection between a first function of controlling the X-ray irradiation by the foot switch 64 alone and a second function of controlling the X-ray irradiation by involving both the on/off state of the foot switch 64 and the moving/stopping state of the catheter 4. In the sixth embodiment, a selection switch for this selection is further provided.

In addition, the X-ray diagnostic apparatus 200 may further include two operation switches composed of operation switches A and B, which turn on or turn off the X-ray irradiation in response to the user's operation. In this case, the operation switch A can independently switch on/off the X-ray irradiation regardless of whether the catheter 4 is moving or stopped. The operation switch B is configured to switch on/off the X-ray irradiation by involving both the on/off state of the operation switch B itself and the moving/stopping state of the catheter 4, similarly to the operation switch in the first and other embodiments. The on/off of the X-ray irradiation based on the moving/stopping state of the catheter 4 is implemented by the X-ray control function F03. The operation switch A is one example of the first operation switch. The operation switch B is one example of the second operation switch.

Moreover, the X-ray diagnostic apparatus 200 may further include another switch for forcibly stopping the display of the reproduced images and forcibly restarting X-ray fluoroscopic imaging, aside from the above-described operation switches. In such a configuration, regardless of the operation of the catheter 4, the user U can view the actual fluoroscopic images of the object P before operating the catheter 4, for example.

According to at least one embodiment described above, exposure to X-rays in a period during which the user performs an operation to insert the device into the object can be reduced.

While certain embodiments have been described, these embodiments have been presented by way of example only, and are not intended to limit the scope of the invention. Indeed, the novel methods and systems described herein may be embodied in a variety of other forms; furthermore, various omissions, substitutions, changes, and combinations of embodiments in the form of the methods and systems described herein may be made without departing from the spirit of the invention. The accompanying claims and their equivalents are intended to cover such forms or modifications as would fall within the scope and spirit of the invention.

What is claimed is:

1. An X-ray diagnostic apparatus configured to communicate with a controller configured to operate a catheter robot capable of inserting a device into an object and moving the device within the object, the X-ray diagnostic apparatus comprising:
   a display configured to be able to display at least one fluoroscopic image of an object; and
   processing circuitry configured to
      receive a control signal indicating a content of an operation on the catheter robot from the controller,
      acquire a plurality of fluoroscopic images of the object by irradiating the object with X-rays,
      control X-ray irradiation to the object,
      cause the display to display the plurality of fluoroscopic images to be sequentially acquired when the X-ray irradiation is performed, and
      generate a plurality of reproduced images based on the plurality of fluoroscopic images acquired before a stop of the X-ray irradiation and cause the display to display the plurality of reproduced images when the X-ray irradiation is stopped.

2. The X-ray diagnostic apparatus according to claim 1, wherein the processing circuitry is configured to:
   perform the X-ray irradiation when the control signal indicates that the device is moving within the object; and
   stop the X-ray irradiation when the control signal indicates that the device is stopped within the object.

3. The X-ray diagnostic apparatus according to claim 1, further comprising an operation switch configured to turn on or turn off the X-ray irradiation in response to a user's operation,
   wherein the processing circuitry is configured to:
      perform the X-ray irradiation to the object when the operation switch is turned on and the control signal indicates that the device is moving within the object; and
      stop the X-ray irradiation when the control signal indicates that the device is stopped within the object, regardless of an on/off state of the operation switch.

4. The X-ray diagnostic apparatus according to claim 3, wherein the processing circuitry is configured to restart the X-ray irradiation when the device starts moving within the object after a stop of the X-ray irradiation due to a stop of device within the object.

5. The X-ray diagnostic apparatus according to claim 1, wherein:

the plurality of reproduced images are the plurality of fluoroscopic images of at least one heartbeat of the object acquired before a stop of the X-ray irradiation; and the processing circuitry is configured to repeatedly reproduce and display the plurality of fluoroscopic images of the at least one heartbeat on the display in a period during which the X-ray irradiation is stopped.

6. The X-ray diagnostic apparatus according to claim 5, wherein the processing circuitry is configured to:

acquire electrocardiographic information of the object; and adjust a reproduction cycle of the plurality of reproduced images corresponding to a heartbeat cycle based on the electrocardiographic information.

7. The X-ray diagnostic apparatus according to claim 6, wherein the processing circuitry is configured to shorten or extend the reproduction cycle of the plurality of reproduced images corresponding to the heartbeat cycle based on the electrocardiographic information.

8. The X-ray diagnostic apparatus according to claim 6, wherein the processing circuitry is configured to adjust the reproduction cycle of the plurality of reproduced images in such a manner that the reproduction cycle of the plurality of reproduced images matches the heartbeat cycle based on the electrocardiographic information.

9. The X-ray diagnostic apparatus according to claim 1, wherein:

the plurality of reproduced images are the plurality of fluoroscopic images of at least one heartbeat of the object acquired before a stop of the X-ray irradiation; and the processing circuitry is configured to repeatedly reproduce and display the plurality of fluoroscopic images of the at least one heartbeat on the display in a period during which the X-ray irradiation is stopped.

10. The X-ray diagnostic apparatus according to claim 9, wherein the processing circuitry is configured to:

acquire respiration information of the object; and adjust a reproduction cycle of the plurality of reproduced images corresponding to a respiration cycle based on the respiration information.

11. The X-ray diagnostic apparatus according to claim 10, wherein the processing circuitry is configured to adjust the reproduction cycle of the plurality of reproduced images in such a manner that the reproduction cycle of the plurality of reproduced images matches the respiration cycle based on the respiration information.

12. The X-ray diagnostic apparatus according to claim 1, wherein the processing circuitry is configured to adjust time length for acquiring the plurality of fluoroscopic images depending on a method of a surgical operation and a target site of the object.

13. The X-ray diagnostic apparatus according to claim 1, wherein the processing circuitry is configured to be able to adjust a reproduction speed of the plurality of reproduced images.

14. The X-ray diagnostic apparatus according to claim 1, further comprising an operation switch configured to turn on or turn off the X-ray irradiation in response to a user's operation, wherein, when the X-ray irradiation is turned off in response to the user's operation on the operation switch, the processing circuitry causes the display to display a still image that is one of:

a most recently acquired fluoroscopic image;

a reproduced image displayed on the display at a time at which the X-ray irradiation is ended; and a reproduced image of a predetermined heartbeat phase.

15. The X-ray diagnostic apparatus according to claim 1, wherein:

the X-ray diagnostic apparatus can further communicate with a drive apparatus that performs driving of a peripheral device except the controller or driving of another medical apparatus except the X-ray diagnostic apparatus; and the processing circuitry is configured to receive a driving signal indicating a content of the driving from the drive apparatus, perform the X-ray irradiation to the object when the driving signal indicates that the peripheral device or the another medical apparatus is being driven; and stop the X-ray irradiation when the driving signal indicates that neither the peripheral device nor the another medical apparatus is being driven.

16. The X-ray diagnostic apparatus according to claim 1, further comprising:

an operation switch configured to turn on or turn off the X-ray irradiation in response to a user's operation; and a selection switch configured to select whether to control on/off of the X-ray irradiation by involving both an on/off state of the operation switch and a moving/stopping state of the device.

17. The X-ray diagnostic apparatus according to claim 1, further comprising:

a first operation switch configured to turn on or turn off X-ray irradiation in response to a user's operation; and a second operation switch configured to turn on or turn off the X-ray irradiation in response to a user's operation, wherein:

on/off of the X-ray irradiation by the first operation switch can be switched independently of on/off of the X-ray irradiation by the processing circuitry based on a moving/stopping state of the device; and the second operating switch is configured to control on/off of the X-ray irradiation by involving both an on/off state of the second operating switch and the moving/stopping state of the device.

18. An X-ray diagnostic system comprising: an X-ray diagnostic apparatus; and a catheter robot that includes a robot main-body and a controller, the robot main-body being able to insert a device into an object and move the device within the object, the controller being able to operate the robot main-body, wherein the X-ray diagnostic apparatus comprises:

a display configured to be able to display at least one fluoroscopic image; and processing circuitry configured to receive a control signal indicating a content of an operation on the catheter robot from the controller, acquire a plurality of fluoroscopic images of the object by irradiating the object with X-rays, control X-ray irradiation to the object, cause the display to display the plurality of fluoroscopic images to be sequentially acquired when the X-ray irradiation is performed, and generate a plurality of reproduced images based on the plurality of fluoroscopic images acquired before a stop of the X-ray irradiation and cause the display to display the plurality of reproduced images when the X-ray irradiation is stopped.

19. The X-ray diagnostic system according to claim 18, wherein the processing circuitry is configured to:

perform the X-ray irradiation when the control signal indicates that the device is moving within the object; and stop the X-ray irradiation when the control signal indicates that the device is stopped within the object.

20. The X-ray diagnostic system according to claim 18, wherein:

the X-ray diagnostic apparatus further comprises an operation switch configured to turn on or turn off the X-ray irradiation in response to a user's operation; and the processing circuitry is configured to:

perform the X-ray irradiation to the object when the operation switch is turned on and the control signal indicates that the device is moving within the object; and stop the X-ray irradiation when the control signal indicates that the device is stopped within the object, regardless of an on/off state of the operation switch.

* * * * *